United States Patent
Persson

(10) Patent No.: US 10,932,959 B2
(45) Date of Patent: Mar. 2, 2021

(54) ABSORBENT ARTICLE WITH AN OIL COMPOSITION AND AN OIL PROTECTING LAYER

(71) Applicant: Essity Hygiene and Health Aktiebolag, Gothenburg (SE)

(72) Inventor: Charlotte Persson, Gothenburg (SE)

(73) Assignee: Essity Hygiene and Health Aktiebolag, Gothenburg (SE)

(*) Notice: Subject to any disclaimer, the term of this patent is extended or adjusted under 35 U.S.C. 154(b) by 0 days.

(21) Appl. No.: 16/313,341

(22) PCT Filed: Jun. 27, 2016

(86) PCT No.: PCT/SE2016/050633
§ 371 (c)(1),
(2) Date: Dec. 26, 2018

(87) PCT Pub. No.: WO2018/004400
PCT Pub. Date: Jan. 4, 2018

(65) Prior Publication Data
US 2019/0159944 A1    May 30, 2019

(51) Int. Cl.
| A61F 13/511 | (2006.01) |
| A61L 15/34 | (2006.01) |
| A61L 15/48 | (2006.01) |
| A61F 13/513 | (2006.01) |
| A61F 13/51 | (2006.01) |

(52) U.S. Cl.
CPC ...... *A61F 13/51113* (2013.01); *A61F 13/513* (2013.01); *A61F 13/5116* (2013.01); *A61L 15/34* (2013.01); *A61L 15/48* (2013.01); *A61F 2013/51026* (2013.01); *A61F 2013/51338* (2013.01)

(58) Field of Classification Search
CPC .............. A61F 13/51113; A61F 13/513; A61F 13/8405; A61F 2013/51117; A61F 2013/51026; A61F 2013/5103; A61F 2013/51059; A61F 2013/51066; A61F 2013/51073; A61F 2013/51338; A61F 2013/8455; A61F 2013/8458; A61F 2013/8461; A61F 2013/8464
See application file for complete search history.

(56) References Cited

U.S. PATENT DOCUMENTS

| 4,263,363 A | 4/1981 | Buck et al. |
| 5,490,846 A * | 2/1996 | Ellis ........................ D04H 1/54 |
| | | 604/366 |
| 6,570,054 B1 | 5/2003 | Gatto et al. |
| 6,756,520 B1 | 6/2004 | Krzysik et al. |
| 7,771,735 B2 * | 8/2010 | Dvoracek ........... A61F 13/8405 |
| | | 424/402 |
| 2004/0122394 A1 * | 6/2004 | Fell .................... A61F 13/15634 |
| | | 604/378 |
| 2011/0159061 A1 | 6/2011 | Warren |

FOREIGN PATENT DOCUMENTS

| CN | 1328438 A | 12/2001 |
| CN | 201551459 U | 8/2010 |
| CN | 105407850 A | 3/2016 |
| EP | 1225276 A1 | 7/2002 |
| EP | 1444969 A1 | 8/2004 |
| JP | 01192803 A | 8/1989 |
| JP | 0956748 A | 3/1997 |
| JP | 2013066598 A | 4/2013 |
| JP | 2013515589 A | 5/2013 |
| WO | 0010500 A1 | 3/2000 |
| WO | 0019955 A1 | 4/2000 |
| WO | 0234305 | 5/2002 |
| WO | 02051456 A2 | 7/2002 |
| WO | 02060502 | 8/2002 |
| WO | 03065951 A2 | 8/2003 |
| WO | 2011082025 A1 | 7/2011 |

OTHER PUBLICATIONS

International Preliminary Report on Patentability for Application No. PCT/SE2016/050633, dated Oct. 4, 2018—8 pages.
International Search Report and Written Opinion for International Application No. PCT/SE2016/050633, dated Mar. 27, 2017—16 pages.
Japanese Notice of Reasons for Rejection for Japanese Application No. 2018-563507, dated Oct. 21, 2019 with translation, 10 pages.
Extended European Search Report for European Application No. 16 907 476.2 dated Feb. 21, 2020, 6 pages.
Chinese Patent Office, Office Action issued in CN 201680087188.5 dated Sep. 15, 2020 and English Translation (13 pages).

* cited by examiner

*Primary Examiner* — Catherine L Anderson
(74) *Attorney, Agent, or Firm* — Wood Herron & Evans LLP

(57) ABSTRACT

The present disclosure relates to a sanitary article such as a sanitary napkin, a panty liner, a diaper or an incontinence pad, including a liquid permeable topsheet, a backsheet, an absorbent core enclosed between the topsheet and the backsheet, and a fibrous layer positioned between the topsheet and the absorbent core. The topsheet includes a coating having a) an oil composition and b) one or more surface active agent(s) including a non-ionic surfactant, wherein the weight ratio of the oil composition and the surface active agent(s) is at least 1:1, and wherein the oil composition is present in an amount of at least 0.3 g/m² of the topsheet and wherein the fibrous layer is an oil protecting layer consisting essentially of non-absorbent fibers.

16 Claims, No Drawings

ABSORBENT ARTICLE WITH AN OIL COMPOSITION AND AN OIL PROTECTING LAYER

CROSS REFERENCE TO RELATED APPLICATIONS

This is a U.S. National Phase application of PCT/SE2016/050633, filed Jun. 27, 2016, the disclosure of which is incorporated herein by reference in its entirety for all purposes.

TECHNICAL FIELD

The disclosure pertains to a sanitary article, such as a sanitary napkin, a panty liner, a diaper or an incontinence pad and the like. In particular, this disclosure pertains to a sanitary article, such as a sanitary napkin, a panty liner, a diaper or an incontinence pad and the like including an oil composition for enhancing the softness of the sanitary article and providing a skin beneficial effect to the user.

BACKGROUND

Sanitary articles of the kind to which this disclosure relates are worn against the skin and include a topsheet, an absorbent core and a backsheet layer. All uses of products which are applied in direct contact with the skin may lead to unwanted side-effects. These may occur as a result of occlusion, moisture and mechanical factors which all, to different degrees, interact and amplify the influence of each other and may cause different forms of skin irritation to users of said articles. While the body facing material is made of a soft, compliant material, the material rubs against the skin during use and may not leave the skin completely dry and free of the bodily fluids.

During frequent insults of bodily fluids and frequent use of disposable absorbent articles, the skin can become irritated, appear red, and be sore to the touch. Creams, lotions, or ointments can be used to provide an artificial hydrophobic barrier on the skin and to treat skin conditions such as diaper rash. However, the use of such hydrophobic compositions has a negative impact on the absorbency performance of the articles. To avoid this side effect, hydrophobic compositions are often applied in relatively low amounts and in different patterns on the topsheet, such as in elongated strings extending in parallel over the topsheet.

Separate application of creams, lotions and ointments to the skin is often messy and inconvenient. Often, these products are not used prophylactically and are only used when signs of diaper rash are visible.

SUMMARY

It is desired to provide a sanitary article with an improved skin care effect and with a high absorbency performance. As such, the present disclosure relates to a sanitary article such as a sanitary napkin, a panty liner, a diaper or an incontinence pad, including a liquid permeable topsheet, a backsheet, an absorbent core enclosed between the topsheet and the backsheet and a fibrous layer positioned between the topsheet and the absorbent core. The topsheet includes a coating comprising a) an oil composition and b) one or more surface active agent(s) including a non-ionic surfactant, wherein the weight ratio of the oil composition to the surface active agent(s) is at least 1:1, and wherein the oil composition is present in an amount of at least 0.3 g/m² of the topsheet. Furthermore, the fibrous layer is an oil protecting layer consisting essentially of non-absorbent fibers.

It has been found that when an amount of oil of at least 0.3 g/m² of the total surface area of the topsheet is present on the topsheet a softer feel against the skin of the user by decrease the friction and chafing of the topsheet material against the skin. Additionally, an enhanced skin care effect may be observed. This is believed to be the result of a long term transfer of the oil from the topsheet to the skin providing a soothing, smoothing and protecting effect for the skin. The fact that the weight ratio of the oil composition to the surface active agent(s), including a non-ionic surfactant, is at least 1:1 allows this relatively high amount of oil to be present on the topsheet while maintaining an efficient liquid inlet.

That the weight ratio of the oil composition to the surface active agent(s) is at least 1:1, means that there is at least as much of the oil composition present as there is of the surface active agent, based on weight.

While the high amount of oil being present on the topsheet provides a silky and soft feel against the user skin and additionally a skin beneficial effect to the user, it has been discovered that there is a risk of the oil migrating down into the sanitary article, and more specifically, to the absorbent core, which may impair the absorption properties of the sanitary article.

Optionally, the oil composition is present in an amount within the range of from 0.3 to 5.0 g/m² of the topsheet. Optionally, the oil composition is present in an amount within the range of from 0.3 to 2.0 g/m² of the topsheet.

This has according to the present disclosure been solved by providing an oil protecting layer between the topsheet and the absorbent core, which layer protects the underlying absorbent core by absorbing and retaining the oil in the fibrous structure of the oil protecting layer. This is due to the fact that it consists essentially of non-absorbent fibrous having a high affinity for the oil. The void space provided by the non-absorbent fiber network holds the oil and prevents it to migrate down into the absorbent core.

Optionally, at least 60% of the topsheet surface area includes the coating. Optionally, at least 80% of the topsheet surface area includes the coating. Optionally, at least 98% of the topsheet surface area includes the coating. Optionally, the entire topsheet includes a continuous coating of a) an oil composition and b) one or more surface active agent(s) including a non-ionic surfactant, wherein the weight ratio of oil composition to surface active agent(s) is at least 1:1, and wherein the fibrous layer is an oil protecting layer consisting essentially of non-absorbent fibers.

Optionally, the weight ratio of the oil composition to the surface active agent(s) is within the range of from 1:1 to 5:1. Optionally, the weight ratio of the oil composition to the surface active agent(s) is within the range of from 1:1 to 3:1. Optionally, or the weight ratio of the oil composition to the surface active agent(s) is within the range of from 1:1 to 1.5:1.

Optionally, the weight ratio of the oil composition to the surface active agent(s) is at least 1.1:1, such as within the range of from 1.1: to 3:1, or within the range of from 1.1:1 to 1.5:1.

Optionally, the sanitary article is a feminine sanitary napkin or a panty liner.

Optionally, the oil(s) in the oil composition is/are selected from olive oil, almond oil, sunflower oil, rapeseed oil or mixtures thereof.

Optionally, the surface active agent(s) is present in an amount within the range of from 0.3 to 2.0 g/m² of the topsheet.

Optionally, the non-absorbent fibers are thermoplastic polymeric fibers.

Optionally, the thermoplastic polymeric fibers are selected from polyolefins, such as polypropylene and/or polyethylene and blends and combinations thereof.

The fact that the thermoplastic polymeric fibers are selected from polyolefins, such as polypropylene and/or polyethylene, provides the fibers with an increased affinity to the oil.

Optionally, the fibrous oil protecting layer has a basis weight of at least 20 g/m², such as at least 40 g/m², such as from 40 g/m² to 150 g/m², such as from 40 g/m² to 100 g/m²

Optionally, the fibrous oil protecting layer has a thickness of at least about 0.5 mm, such as at least about 1 mm, such as at least about 1.5 mm, or at least about 2 mm. The thickness under load of the fibrous oil protecting layer may also be from about 0.5 to about 5 mm, and is measured according to WSP 120.6, according to method option A, wherein the thickness is measured after removing 1 layer of material from a slitted roll, the material being conditioned 30 minutes before measuring. The pressure used was 0.5 kPa with a presser-foot having an area of 25 cm² and with 10 s waiting before taking the thickness value.

Optionally, the fibrous oil protecting layer has a density within the range of from 0.02 to 0.10 g/cm³, from 0.04 to 0.08 g/cm³ or a density of from 0.04 to 0.06 g/cm³. The fact that the fibrous oil protecting layer has a density within the range of from 0.02 to 0.10 g/cm³ influences the oil retention capacity of the fibrous layer. The amount of oil that may be absorbed and retained, as it determines how much oil that may be held in the structure. The structure may have a density of at least 0.02 g/cm³ in order for the structure to retain the oil and a density up to 0.10 g/cm³ for still providing enough void volume to hold the oil.

Optionally, the fibrous oil protecting layer has a basis weight of at least 20 g/m², such as from 20 g/m² to 150 g/m², optionally at least 35 g/m², such as within the range of from 35 g/m² to 105 g/m².

The thickness and the basis weight of the fibrous oil protecting layer contributes to providing an open and thick structure. This open, thick structure acts as a non-absorbing reservoir for oil containment, which provides protection for the absorbent core.

An improved oil protection for the absorbent core in an absorbent article in accordance with the present disclosure may thus be achieved by the provision of an oil protecting layer which has a sufficiently open structure for holding an oil composition in accordance with the present disclosure, while at the same time being sufficiently dense for retaining the oil captured in the layer. The oil protection may further be enhanced by providing a thicker layer, such as at least 0.5 mm, or at least 1 mm, which increases the distance from the topsheet to the absorbent core, and especially in combination with the given density of the oil protecting layer.

An additional effect of the oil protection layer having a density within the range of from 0.02 to 0.10 g/cm³ and also that the thickness is at least 0.5 mm, or at least 1.0 mm is that the absorbent article becomes softer and has an improved ability to follow the contours of the user body which enhances the contact between the users skin and the absorbent article and thus may improve the oil transfer and reduces the chafing of the topsheet against the user body.

Optionally, the non-absorbent fibers has a dTex within the range of from 3 to 30 dTex.

Optionally, the topsheet is a fibrous topsheet. Optionally, the fibrous topsheet is a spunbond nonwoven including a plurality of thermal bonded points. Optionally, the plurality of thermal bonded points are located in a sparse pattern wherein the pattern includes bonding points having a distance to adjacent bonding points being at least 3 mm, or at least 4.0 mm. The cumulated surface area of the plurality of bonded points may be less than 20% of the total surface area of the topsheet.

Optionally, the topsheet has a basis weight of 22 g/m² or less, such as 20 g/m² or less, such as 19 g/m² or less.

Optionally, the fibrous topsheet consists essentially of non-absorbent fibers. Optionally, the non-absorbent fibers are thermoplastic polymeric fibers, selected from polyolefins, such as polypropylene and/or polyethylene and blends and combinations thereof.

The fact that the fibrous topsheet consists essentially of non-absorbent fibers, including, for example, thermoplastic polymeric fibers, selected from polyolefins, such as polypropylene and/or polyethylene, provides the topsheet with an increased affinity to the oil, this may contribute to increased oil retention onto the topsheet and thus a long-lasting soft feel against the skin.

Optionally, the sanitary article as disclosed herein may be produced by a method including the following steps;

a) preparing the topsheet by applying to the topsheet an emulsion including an aqueous solution including a non-ionic surfactant and an oil, b) optionally, drying the topsheet, c) superposing the topsheet onto said fibrous acquisition layer consisting essentially of non-absorbent fibers, wherein step c) can take place either before step a) or after step b).

DETAILED DESCRIPTION OF PARTICULAR EMBODIMENTS

The present disclosure thus relates to a sanitary article including a liquid permeable topsheet, a backsheet and a fibrous layer enclosed between the topsheet and the backsheet. The topsheet includes a coating including a) an oil composition and b) one or more surface active agent(s) including a non-ionic surfactant, wherein the weight ratio of the oil composition and the surface active agent(s) is at least 1:1, and wherein the oil composition is present in an amount of at least 0.3 g/m² of the total surface area of the topsheet. The fibrous layer enclosed between the topsheet and the backsheet is an oil protecting layer consisting essentially of non-absorbent fibers.

The term "sanitary article" refers to products that are placed against the skin of the wearer to absorb and contain body exudates, like urine, faeces and menstrual fluid, which articles can also be used to deliver pH controlling agents to these areas. The disclosure mainly refers to disposable sanitary articles, which means articles that are not intended to be laundered or otherwise restored or reused as a sanitary article. Examples of disposable sanitary articles include feminine hygiene products such as sanitary napkins, panty liners, sanitary panties and feminine inserts; diapers and pant diapers for infants and incontinent adults; incontinence pads; diaper inserts and the like.

A surfactant according to the present disclosure is a substance which lowers the surface tension of the medium in which it is dissolved, and/or the interfacial tension with other phases, and, accordingly, is positively adsorbed at the liquid/solid and/or at other interfaces. The non-ionic surfactant may be any known non-ionic surfactant suitable for use in hygienic applications, as is generally known in the art.

In certain embodiments, the nonionic surfactant is selected from the group of alkoxylated C6-C8 fatty alcohols, alkoxylated C6-C18 amines, alkoxylated C6-C18 amides, alkoxylated C6-C18 fatty acids, alkoxylated C6-C18 fatty acid esters and alkoxylated C8-C18 alkylphenols and alkoxylated triglycerides of C6-C18 fatty acids and/or the esterification products thereof with fatty acids C8-C18 selected.

The one or more surface active agent(s) may optionally further include at least one anionic and/or a cationic surfactant.

The oil composition may be a vegetable oil and suitable oils are coconut oil, almond oil, walnut oil, peach kernel oil, apricot kernel oil, avocado oil, tea tree oil, soybean oil, sesame oil, sunflower oil, evening primrose oil, rice bran oil, palm kernel oil, mango oil, meadowfoam seed oil, safflower oil, rapeseed oil, macadamia nut oil, grape seed oil, amaranth seed oil, argan oil, bamboo oil, olive oil, wheat germ oil, pumpkin seed oil, mallow oil, hazelnut oil, safflower oil, canola oil, jojoba oil, rose oil, cottonseed oil and/or mixtures of these oils.

The topsheet includes at least 0.3 g/m² of oil composition. The coating may be formed on a topsheet material by applying an aqueous emulsion comprising a nonionic surfactant, one or more further surface active agent(s) and the oil composition to the topsheet, followed by drying of the topsheet material and resulting in a coating formed on the topsheet material.

The weight ratio of the oil composition and the surface active agent(s) is at least 1:1 in the coating according to the present disclosure, such as at least 1.1:1, such as at least 1.5:1.

The coating composition may be applied to the topsheet material by any suitable means including spraying, slot coating, kiss roll coating and/or soaking the material in a bath containing the coating composition. The coating may be performed in-line during assembly of the sanitary article. Alternatively, the topsheet material may be prepared separately and delivered as ready-to-use rolls to the sanitary article manufacturing plant.

The coating may also be formed by a combination of the above methods, meaning that the one or more surface active agent(s) including a nonionic surfactant may be coating by one of the methods including spraying, slot coating, kiss roll coating and/or soaking the material in a bath containing the coating composition above and the oil composition may be coated by a separate method chosen from for example spraying, slot coating, kiss roll coating and/or soaking the material in a bath containing the coating composition.

After the topsheet material has been wetted with the coating composition, the topsheet material is dried by e.g. guiding the topsheet material through a forced hot air oven or across a bank of infrared light or dielectric dryers or other conventional drying apparatuses as are known to the skilled person in the art.

The resulting sanitary article has a soft and creamy texture against the skin, which is the result of the high amount of oil composition which may be applied to the topsheet while preserving a high inlet of liquid into the sanitary article and the absorbent capacity of the absorbent core. The coating may thus be applied by continuously coating at least 60%, or at least 80%, of the topsheet surface area. The coating may for example be applied continuously in the crotch portion such that the topsheet in the front end portion and the back end portion of sanitary article does not comprise any coating, or at least partially does not comprise any coating.

The coating may also be applied continuously over substantially 100% of the surface area of the topsheet.

The oil protecting layer in accordance with the present disclosure is a porous fibrous layer essentially consisting of non-absorbent fibers. The presence of an oil protecting layer as disclosed herein in contact with and underneath the topsheet has been found to maintain efficient absorbent properties of the sanitary article and reduced impact of any oil possibly migrating into the sanitary article. The topsheet may also comprise or consist essentially of non-absorbent fibers. The term "non-absorbent fibers" refers to fibers which do not absorb water to an appreciable extent. Suitable polymers from which the non-absorbent fibers may be formed are non-water-absorbent polymers such as polyolefins, polyesters, polyamides and blends and combinations thereof. The non-absorbent fibers may be monocomponent fibers, bicomponent fibers or multicomponent fibers including polyolefins, polyesters, polyamides and blends and combinations thereof.

As used herein, the oil protecting layer or the topsheet material "consisting essentially" of non-absorbent fibers means that at least 95% of the fibers are non-absorbent fibers, such as at least 99%, such as at least 100% of the fibers in the oil protecting layer or the topsheet material are non-absorbent fibers. The oil protecting layer and the topsheet material may however also include further substances present in small amounts, such as for example binders and pigments, as known by the person skilled in the art.

The thickness according to the present disclosure is measured as a thickness under load of the oil protecting layer, and may be at least about 1 mm, such as at least about 1.5 mm, such as at least about 2 mm. The thickness under load of the acquisition layer may also be from 1.0 to 5.0 mm, and is measured according to WSP 120.6, according to method option A, wherein the thickness is measured after removing 1 layer of material from a slitted roll, the material being conditioned 30 minutes before measuring. The pressure used was 0.5 kPa with a presser-foot having an area of 25 cm² and with 10 s waiting before taking the thickness value.

The fibrous oil protecting layer may have a basis weight of at least 20 g/m², such as from 20 g/m² to 150 g/m², optionally at least 35 g/m², such as within the range of from 35 g/m² to 105 g/m².

A sanitary article according to the disclosure additionally has a lower rewet than comparative example according to the below measurements. The exemplary sanitary article according to the disclosure has a fibrous layer consisting essentially of non-absorbent fibers positioned between said topsheet and said absorbent core, while comparative example is a sanitary article having a pulp layer positioned between said topsheet and said absorbent core instead of a fibrous layer consisting essentially of non-absorbent fibers. The exemplary sanitary article according to the disclosure has a mean value of 0.80 g, while comparative example layer has a mean rewet value of 1.98.

TABLE 1

| Rewet 5 ml | Mean value | Std dev | Min | Max | Count |
|---|---|---|---|---|---|
| Example | 0.80 | 0.19 | 0.58 | 1.05 | 6 |
| Comp. Ex | 1.98 | 0.08 | 1.85 | 2.08 | 6 |

The lower rewet of the sanitary article according to the present disclosure improves the function of the oil composition as the contact between the user skin and the oil composition decreases with a wet topsheet.

The sanitary article in this disclosure includes an absorbent core, arranged between the oil protecting layer and the backsheet. The absorbent core can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbents in an absorbent structure. It is also common to have absorbent structures including layers of different material with different properties with respect to liquid acquisition capacity, liquid distribution capacity and storage capacity. This is well-known to the person skilled in the art and does therefore not have to be described in detail. The thin absorbent bodies, which are common in today's sanitary articles, often include a compressed mixed or layered structure of cellulosic fluff pulp and superabsorbent. The size and absorbent capacity of the absorbent structure may be varied to be suited for different uses such as sanitary napkins, pantyliners, adult incontinence pads and diapers, baby diapers, pant diapers, etc.

The liquid permeable topsheet can be any suitable topsheet material as known by the person skilled in the art and may be fibrous topsheet material composed of a nonwoven material, e.g. spunbonded, meltblown, carded, hydroentangled, wetlaid etc. Suitable nonwoven materials can be composed of natural fibers, such as woodpulp or cotton fibres, synthetic thermoplastic fibres, such as polyolefins, polyesters, polyamides and blends and combinations thereof or from a mixture of natural and synthetic fibres. Further examples of topsheet materials are porous foams. The materials suited as topsheet materials should be soft and non-irritating to the skin and be readily penetrated by body fluid, such as urine or menstrual fluid. The topsheet material may essentially constitute of non-absorbent fibers, such as synthetic thermoplastic fibers, such as such as polyolefins, polyesters, polyamides and blends and combinations thereof. The synthetic fibers may be monocomponent fibers, bicomponent fibers or multicomponent fibers including polyesters, polyamides and/or polyolefins such as polypropylene and polyethylene.

The topsheet may also have a basis weight of 22 $g/m^2$ and less, such as 20 $g/m^2$ and less, such as 19 $g/m^2$ and less. A topsheet being a spunbond nonwoven including a plurality of thermal bonded points has been found to improve the softness of the topsheet and to increase the contact between the oil composition and the user skin. The bonded points may be located in a sparse pattern including bonding points having a distance to adjacent bonding points of at least 3 mm, or at least 4.0 mm. The cumulated surface area of the plurality of bonded points may be less than 20% of the total surface area of the topsheet.

The backsheet may consist of a thin plastic film, e.g. a polyethylene or polypropylene film, a nonwoven material coated with a liquid impervious material, a hydrophobic nonwoven material, which resists liquid penetration. Laminates of plastic films and nonwoven materials may also be used. The backsheet material can be breathable so as to allow vapor to escape from the absorbent structure, while still preventing liquids from passing through the backsheet material.

The invention claimed is:

1. A sanitary article comprising a liquid permeable topsheet, a backsheet, an absorbent core enclosed between said topsheet and said backsheet, and a fibrous oil protecting layer including non-absorbent fibers positioned between said topsheet and said absorbent core, wherein said topsheet comprises a coating comprising a) an oil composition and b) one or more surface active agents including a non-ionic surfactant, wherein the weight ratio of said oil composition and said one or more surface active agents is within the range of from 1:1 to 5:1, wherein said oil composition is a vegetable oil composition, wherein said oil composition is present in an amount within the range of from 0.3 $g/m^2$ to 2.0 $g/m^2$ of said topsheet, wherein said one or more surface active agents is/are present in an amount within the range of from 0.3 to 2.0 $g/m^2$, wherein at least 60% of a surface area of said topsheet comprises said coating, and wherein said oil protecting layer defines a thickness within the range of 1 mm to 5 mm and said oil protecting layer has a density within the range of from 0.02 to 0.10 $g/cm^3$, the thickness and the density of said oil protecting layer resulting in the non-absorbent fibers retaining any oil exiting said oil composition and preventing such oil from migrating into said absorbent core.

2. The sanitary article according to claim 1, wherein the weight ratio of said oil composition and said one or more surface active agents is within the range of from 1:1 to 3:1.

3. The sanitary article according to claim 1, wherein said sanitary article is a feminine sanitary napkin or a panty liner.

4. The sanitary article according to claim 1, wherein said oil composition includes one or more oils selected from the group consisting of olive oil, almond oil, sunflower oil, rapeseed oil and mixtures thereof.

5. The sanitary article according to claim 1, wherein said oil composition is present in an amount within the range of from 0.7 to 2.0 g/m2 of the topsheet.

6. The sanitary article according to claim 1, wherein said non-absorbent fibers are thermoplastic polymeric fibers.

7. The sanitary article according to claim 6, wherein said thermoplastic polymeric fibers include polyolefins selected from the group consisting of polypropylene and polyethylene and blends and combinations thereof.

8. The sanitary article according to claim 1, wherein said fibrous oil protecting layer has a basis weight of at least 20 g/m2.

9. The sanitary article according to claim 1, wherein said topsheet is a fibrous topsheet.

10. The sanitary article according to claim 9, wherein said topsheet is a spunbond nonwoven comprising a pattern of a plurality of thermal bonded points, wherein the pattern includes bonding points having a distance to adjacent bonding points being at least 3 mm.

11. The sanitary article according to claim 9, wherein said fibrous topsheet has a surface weight of 22 g/m2 and less.

12. The sanitary article according to claim 9, wherein said fibrous topsheet consists essentially of non-absorbent fibers.

13. The sanitary article according to claim 12, wherein said non-absorbent fibers of the topsheet include thermoplastic polymeric fibers formed from polyolefins selected from the group consisting of polypropylene and polyethylene and blends and combinations thereof.

14. A method of producing a sanitary article according to claim 1, the method comprising:
   (a) preparing said topsheet by applying to said topsheet an emulsion comprising an aqueous solution comprising a nonionic surfactant and a vegetable oil, such that at least 60% of a surface area of said topsheet comprises said coating; and
   (b) superposing said topsheet onto said oil protecting layer consisting essentially of non-absorbent fibers, wherein step (b) can take place either before step (a) or after step (a), wherein said oil protecting layer defines a thickness within the range of 1 mm to 5 mm.

15. The sanitary article according to claim 1, wherein said oil protecting layer consists essentially of the non-absorbent fibers.

16. The sanitary article according to claim 1, wherein at least 80% of the surface area of said topsheet comprises said coating.

* * * * *